United States Patent [19]

Ling

[11] 4,012,494
[45] Mar. 15, 1977

[54] DIRECT RADIOIMMUNOASSAY FOR ANTIGENS AND THEIR ANTIBODIES

[75] Inventor: Chung-Mei Ling, Highland Park, Ill.

[73] Assignee: Abbott Laboratories, North Chicago, Ill.

[22] Filed: June 17, 1974

[21] Appl. No.: 480,180

Related U.S. Application Data

[63] Continuation-in-part of Ser. No. 210,510, Dec. 21, 1971, Pat. No. 3,867,517.

[52] U.S. Cl. .................................. 424/1; 23/230 B; 424/12; 424/1.5
[51] Int. Cl.$^2$ ................. G01N 33/00; G01N 33/16; G21H 5/02
[58] Field of Search .................... 424/1, 12, 1.5; 23/230 B, 259

[56] References Cited

UNITED STATES PATENTS

| | | | |
|---|---|---|---|
| 3,646,346 | 2/1972 | Catt | 424/1 X |
| 3,790,663 | 2/1974 | Garrison et al. | 424/12 |
| 3,867,517 | 2/1975 | Ling | 424/1 |

OTHER PUBLICATIONS

Catt, Acta Endocrinologica Supplementom, No. 142, 1969.
Salmon et al., The Journal of Immunology, vol. 103, No. 1, July, 1969.
Salmon et al., The Journal of Immunology, vol. 104, No. 3, Mar., 1970.
Kirkham et al., Radioimmunoassay Methods, 1971.
Haberman, Z. Klin. Chem. u. Klin. Biochem., vol. 8, Jan. 1970, pp. 51–55.
Haberman, Radioimmunoassay and Related Procedures in Medicine, vol. I, IAEA, Vienna, 1974, pp. 341–353.
Koutoulidis et al., Radioimmunoassay and Related Procedures in Medicine, vol. II, IAEA, Vienna, 1974, pp. 377–383.

*Primary Examiner*—Benjamin R. Padgett
*Assistant Examiner*—Christine M. Nucker
*Attorney, Agent, or Firm*—Robert D. Weist; Robert L. Niblack

[57] ABSTRACT

A method for direct radioimmunoassay of antigens or their associated antibodies utilizing a coated test apparatus comprising adding a serum to be tested for an antigen to test apparatus coated with its antibody; incubating the tubes for from 0.5 to 42 hours; aspirating the contents and washing the same with a Tris-HCl and sodium azide mixture; adding purified $I^{125}$ labeled antibody into the tube and incubating for from 1 to 24 hours; aspirating and washing the contents; and counting the tube for $I^{125}$ radiation. A similar assay for the antibody may be conducted utilizing an antigen coated apparatus and $I^{125}$ labeled antigen. The method for coating these apparatus such as tubes comprises adding the antigen or antibody solution in a Tris-HCl, sodium azide solution into a suitable test tube or well, incubating the tubes at room temperature, aspirating and washing the contents and storing at from between 2° and 25° C. until use.

11 Claims, 1 Drawing Figure

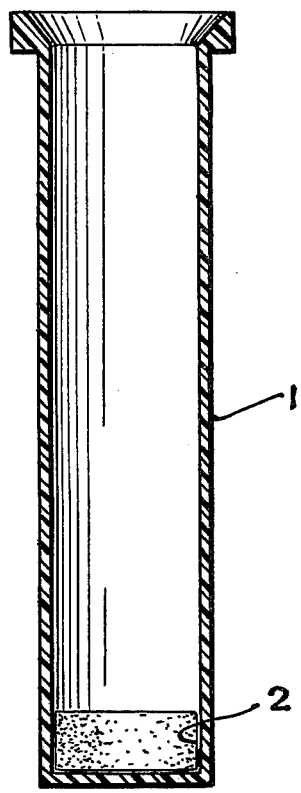

DIRECT RADIOIMMUNOASSAY FOR ANTIGENS AND THEIR ANTIBODIES

This application is a Continuation-in-Part of U.S. Ser. No. 210,510 filed Dec. 21, 1971, now U.S. Pat. No. 3,867,517.

BACKGROUND OF THE INVENTION

This invention relates to a diagnostic method for the radioimmunoassay of antigens and their antibodies and a method for coating apparatus useful in the above determination. More particularly, this invention relates to a direct method for determining hepatitis associated antigens or their antibodies and is also directed toward a method for preparing diagnostic apparatus suitable for use in the same.

Although there have been methods for determining the presence of antigenically active macromolecules such as intact viruses, virus capsids, virus subunits, bacteria, membranes, cell walls, hormones, etc., there have been a lack of a simple, yet sensitive, test method and apparatus for determining the presence of these materials. Viral hepatitis, including so-called serum hepatitis, which is a relatively common disease, has not been heretofore easily detected by a sensitive test which is both specific and reproducible for quickly determining whether or not the sera from a patient or a donor contains hepatitis associated antigens or antibodies.

Furthermore, radioimmunoassay techniques have been developed in the past for various antigen-antibody materials; however, these radioimmunoassay techniques such as disclosed in articles by Keven Catt et al in the *Journal of Biochemistry*, 1966, Volume 100, pages 31c and 33c and in *Science*, Volume 158, page 1570, 167, are an indirect radioimmunoassay technique wherein the amount of antigen present in roughly inversely proportional to the amount of radiation emitted by the tracer material. These procedures required the use of correlation tables and other materials which generally rendered the results less than reproducible and exact. Wide, *Karolinska Simposia*, 1st Simposia, Sept. 23 to 25, 1969, University Hospital Upsila, Sweden, pages 207 to 214 discloses a radioimmunoassay wherein an allergen is absorbed on a plastic polymer and reagin is bound immunochemically to the solid phase allergen and then labeled anti-reagen is bound to the reagin.

Briefly, it has been discovered that the above-noted difficulties, i.e., lack of reproducibility and exactness, have been overcome by utilizing the method of the present invention. Briefly, in one application, the method of the present invention comprises contacting an unknown serum sample with an antibody coated implement, incubating the test implement and serum for a period of from 0.5 to 42 hours, aspirating and washing, contacting an $I^{125}$ labled antibody with the serum and coated with the test apparatus and incubating for from 1 to 6 hours, aspirating and washing, and counting the tube for $I^{125}$ gamma radiation.

It is therefore the principal object of the present invention to provide a novel method for the direct determination of antigens and their antibodies.

It is a further object of the present invention to provide a method for coating diagnostic apparatus for use in radioimmunoassay determinations.

It is a still further object of the present invention to provide a method for quickly and accurately determining the presence of hepatitis associated antigens or antibodies in sera.

Still further objects and advantages of the diagnostic method for direct radioimmunoassay and method for coating test implements useful in the same will become more apparent from the following more detailed description thereof and the following attached drawing wherein:

The drawing is a cut-away view of a coated test implement useful in the method of the present invention.

The drawing shows a test tube shaped test implement 1 with a coated portion 2. Coated portion 2 has a coating of an antigen or its antibody preferably located as shown, i.e., in the bottom of the tube. Although the drawing shows one embodiment of apparatus suitable for use in performing the method of the present invention, the method of this invention should not be limited thereto. Other solid state devices may be employed such as inserts as disclosed in copending U.S. application Ser. No. 210,511 filed Dec. 21, 1971, discs, spherical beads or particles, and the like, all of which may be coated with an antigen or antibody.

Coated portion 2 is coated with ether an antigen or an antibody depending on the material to be tested. The antibody or antigen can be affixed to the test apparatus by contact coating from solution or any other means, the manner of affixation not being critical. Since the method is similar with regard to almost all antigens and antibodies, the process for coating these tubes will be described with reference to a particular hepatitis associated antibody, i.e., anti-Australia antigen. A solution of anti-Australia antigen having a concentration of from about 1 to about 100 micrograms of protein per ml. is prepared from an anti-Australia antigen serum in from about 0.005 to about 0.02 molar Tris-HCl, i.e., 2-amino-2-hydroxymethyl-1,3-propanediol-HCl. The Tris-HCl buffers the solution to a pH of from about 7.1 to about 9.5 together with from about 0.01% to about 0.05% sodium azide. This anti-Australia antigen solution is then coated on the tube surfaces and incubated at room temperature for from 6 to 72 hours and preferably for from 12 to 48 hours. These coated tubes are then washed with from about 0.005 to about 0.02 molar Tris-HCl at a pH of 6.9 to 8.4 plus from about 0.01% to about 0.05% sodium azide. Following this washing and rinsing step, the test implements may be stored at 4° C. until necessary for use for radioimmunoassay. For additional details for methods of preparing antigen or antibody or the affixing of such to tubes or other apparatus, reference can be made to the publication by C. M. Ling and L. R. Overby, "Prevalence of Hepatitis B Antigen as Revealed by Direct Radioimmunoassay with $I^{125}$ Antibody," the *Journal of Immunology*, Volume 109, No. 4, October 1972.

It is preferred to utilize an 0.01 molar solution of Tris-HCl and 0.02% sodium azide buffered at a pH of 7.1 for both the incubation medium and the washing medium.

The amount of antibody or antigen coated in the tubes is not critical since the test is run each time in comparison with at least one blank test. No standard curves or charts are necessary for the test of the present invention; therefore, no specific amount of antibody or antigen in the coating is required as long as two similar tubes are used.

Although the coating method has been described with reference to a coated tube, the coating method may be utilized to prepare coated inserts, beads, or any apparatus for use with wells, etc. by dipping the inserts in the antigen or antibody solution and following the remaining procedure. Likewise, while generally described in terms of coating of a tube, the antibody or antigen can be affixed to the test apparatus to provide a layer of the antibody or antigen, using any suitable method for achieving bonding or attachment thereto. The time required for incubating the affixed antigen or antibody to the test apparatus is not critical and may be as low as about 10 minutes. However, where a coated tube is used, production processes dictate that a period of 6 to 72 hours is preferred.

Antigens and antibodies which may be determined by means of the method of the present invention include: various intact viruses, virus capsids, virus subunits, bacteria, membranes, cell walls, various hormones, gamma globulins, etc. The only requirement with regard to the above materials is that the materials have a minimum of two antigenically active sites. Furthermore, antigens and antibodies having multiple combining sites are detectable even in the presence of their respective antibodies and antigens, provided a minimum of two free combining sites remain available. Although the radioimmunoassay method of the present invention is useful for detecting the above class of materials, it is especially well adapted, and this is a preferred embodiment of the present invention, for the determination of the presence of hepatitis associated antigens and antibodies, such as Australia antigen and anti-Australia antigen.

While the radioimmunoassay method of the present invention has been briefly described above, the method will now be described with reference to the specific materials and steps necessary for conducting the direct radioimmunoassay technique for determining the presence of the hepatitis associated antigen, Australia antigen.

First, a measure sample of plasma or blood to be tested for hepatitis associated antigen is placed in an anti-Australia antigen or antibody coated tube. The material is incubated for a period of from 0.5 to 42 hours at room temperature and preferably for from 12 to 24 hours. The coated material is washed with the buffer mixture, i.e., Tris-HCl and sodium azide or with distilled or deionized water. A measured amount of purified $I^{125}$ labeled anti-Australia antigen is then added to the tube or test receptacle well and the tube or insert in contact therewith is incubated for an additional 1 to 24 hours at room temperature and preferably for from 1.5 to 6 hours. Following this incubation, the contents are washed utilizing the buffer mixture or distilled or deionized water and the tube is placed in the well of a counter which is capable of counting gamma radiation. Background controls in duplicate are run simultaneously utilizing a normal plasma in place of the tested plasma and tested in a similar manner. If the unknown plasma has a higher count rate than the background, it is considered hepatitis associated antigen positive.

Generally, it is preferred to utilize a counting time of one minute, however, if a sample is quite close to the upper limit of the control, a longer counting time up to ten minutes may be utilized in order to obtain exact counting results.

As noted above, the incubations are generally conducted at room temperature although slight warming up to about 35° C. may be utilized to shorten the incubation time. Where a short incubation time is desirable as a means of reducing the total time required to conduct the test procedure, the incubation time can be greatly reduced by increasing the reaction temperature to from about 35° to 55° C., especially from 38° to 50° C., with about 45° C. being most preferred. Use of the foregoing higher temperatures can effectively reduce the incubation time to about 1/6 to 3 hours, especially about 1 to about 2 hours. For example, in the procedure described above, after the plasma or blood to be tested is placed in the coated tube, or other apparatus, the incubation time can be greatly reduced to about two hours by incubating at about 45° C. rather than at room temperature. After incubation, the plasma or blood sample is removed from the test apparatus and rinsed with distilled or deionized water, the washing procedure being preferably repeated. Labeled antibody is then added to the test apparatus and the apparatus incubated at about 45° C. for about one hour. At the end of the hour, the antibody solution is removed from the test apparatus which is then rinsed with distilled or deionized water as previously described. The test apparatus is subsequently placed in a suitable well-type gamma scintillation counter and the count rate determined. The presence or absence of antigen in the plasma or blood sample is then determined by relating net counts per minute of the unknown sample to net counts per minute of a negative control sample.

To determine the presence of an antibody in a sample, the procedure is reversed by instead affixing to the test apparatus a suitable antigen. As described, the sample is then placed in contact with the apparatus having an antigen layer whereby any antibody in the sample will bond to the antigen. After washing, a suitably labeled antigen is then placed in contact with the apparatus to bond the labeled antigen to the antibody being measured. The radioactivity is then measured as previously described to determine the presence or absence of antibody.

While an incubation temperature of from about 35° to 55° C. can be employed as a means of reducing the incubation time, incubation temperatures greater than 55° C. and especially 60° C. are undesirable since activity drops off rapidly because of the destruction or denaturing of the reagents which is believed to occur at these temperatures, i.e., the layer of antigen or antibody becoming disassociated from the test apparatus, as well as denaturing of the labeled antibody or antigen.

Short incubation times are desirable since rapid completion of the test procedure is permitted. In the collection and use of human blood for example, two to three hour incubation periods permit the collection, testing and use of blood, all within the same day. As used herein, the term "deionized" water is taken to mean water where the ions of any impurities have been removed by any conventional means.

Generally, the buffer medium contains from about 0.005 to about 0.02 molar Tris-HCl and from about 0.01 to 0.05% by weight sodium azide at a pH of 6.9 to 8.4. The preferred buffer comprises 0.01 molar Tris-HCl and 0.02% by weight sodium azide.

Generally, the tests are run using undiluted blood serum or plasma, however, if samples are limited, a suitable dilution of the sample in normal serum or plasma, such as bovine serum albumen or in a buffer mixture, such as a mixture of Tris-HCl and sodium azide, a mixture of Tris-HCl, sodium azide and 1% bovine serum albumen, etc. may be used.

Also, although the method of the present invention has been described with reference to $I^{125}$ tagged antigens or antibodies, the preferred radioactive material, any radioisotope generally used for tagging or tracing antigens or antibodies in radioimmunoassay procedures may be utilized. $I^{125}$ labeled iodine is preferred because of its long sixty day half life. Other radioisotopes that can be utilized include $I^{131}$ having an eight day half life, $P^{32}$ having a fourteen day half life, as well as other radioisotopes such as Tritium. Mixtures of the above can also be employed.

As noted above, the process of the present invention utilizes a direct radioimmunoassay technique for the determination of various antigens and their antibodies, especially hepatitis associated antigen or its antibody. Furthermore, if a quantitative determination of hepatitis associated antigen is desired, a standardized curve directly showing the relationship between counts per minute and the amount of hepatitis associated antigen may be utilized.

The foregoing methods and the apparatus of the present invention will now be illustrated by the following specific example which is for the purpose of illustration only and is not to be taken as limiting. In the following example all parts and percentages are by weight and all temperatures in degrees centigrade.

EXAMPLE I

The tube as shown in the drawing which is molded from polystyrene or polypropylene is coated with a purified hepatitis associated antibody. This coating is applied by subjecting the surface of the tube to a diluted solution of hepatitis associated antibody in 0.01 molar Tris-HCl at a pH of 7.1 and 0.02% by weight sodium azide and the coated tube is incubated at room temperature for one day. The tube is then washed with aliquots of 0.01 molar Tris-HCl plus 0.02% by weight sodium azide. These tubes may be stored at 4° C. until use. Three 100 microliter plasma samples are placed on each in three separate coated tubes, each tube being coated with hepatitis associated antibody. One of these plasma samples is the unknown, the other two are negative for hepatitis associated antigen. Each step in the procedure is applied to each of the three samples. The two negative samples provide the background radiation against which the unknown sample is ultimately compared. These samples are then set aside and incubated for 18 hours at room temperature. At the end of this time, the coated tubes are washed with aliquots of the incubation buffer mixture or water. At this time, 2.5 nanograms of purified $I^{125}$ labeled hepatitis associated antibody in 0.1 ml. volume are placed into each coated tube. The tubes are again set aside and incubated for two hours after which time the tube is washed again with water or aliquots of the incubation buffer mixture. Each of the negative plasma samples is counted utilizing a conventional radiation counter having a well and capable of detecting gamma radiation. The negative samples are counted for 1 minute and the average number of counts per minute is determined; in this case, 200 counts per minute. The unknown sample is then counted in the same manner and compared with the average value of counts per minute of the negative plasma samples plus a correction factor equal to 50% of the counts per minute of the negative sample. The unknown plasma in this case has a count rate of 400 counts per minute which is above the 300, i.e., 200 plus 50% of 200 = 300, which is the maximum for a negative test.

EXAMPLE II

The following is an example of a test procedure employing a short incubation time and described with reference to the detection of hepatitis associated antigen.

0.1 ml. of serum to be tested is added to the bottom of an antibody coated tube, ensuring that the serum is evenly distributed therein. The tube is placed in a water bath maintained at about 45° C. to incubate for a period of 2 hours. The contents of the tube are then aspirated to remove the serum and washed with distilled or deionized water or with an aliquot of a prepared rinse solution comprising trimethamine buffer diluted with deionized or distilled water. The washing process is repeated four additional times. 0.1 ml. $I^{125}$ labeled hepatitis associated antibody solution is then added to the bottom of each tube, again ensuring even distribution of the labeled antibody. The tube is then incubated at about 45° C. for one hour. Thereafter, the contents are aspirated in order to remove any unbound labeled antibody and the tube is rinsed five times as previously described. The tube is subsequently placed in a suitable well-type gamma scintillation detector and the net counts per minute determined. To obtain the net counts per minute, any machine or background count is deducted from the total counts per minute obtained for the sample. The actual radioactivity of the sample is thus obtained which is a direct measure of the antigen present in the sample.

As is evident, the above-noted test procedures provide a simple yes — no test for determining the presence or absence of hepatitis associated antigen in an unknown sample of blood or plasma. Although some correction factor is required, the test is quite conclusive and reproducible and has a high degree of accuracy.

While the process of the present invention has been illustrated by way of foregoing specific example, the process of the present invention should be in no way limited thereto but should be construed as broadly as any and all equivalents in the appended claims.

What is claimed is:
1. A method for determining the presence of a hepatitis associated antigen or its antibody in an unknown sample utilizing direct radioimmunoassay comprising:
   a. forming a solution of a hepatitis associated antigen or antibody;
   b. affixing the antigen or antibody contained in said solution to a test apparatus;
   c. incubating said test apparatus to affix said antigen or antibody to said test apparatus as a first layer;
   d. washing said incubated affixed test apparatus to remove any unaffixed antigen or antibody;
   e. placing said unknown sample in contact with said incubated and washed test apparatus;
   f. including said unknown sample while in contact with said washed test apparatus to bond any of said antibody or antigen present in said unknown sample as a second layer to said antigen or antibody layer on said test apparatus, respectively;
   g. washing said incubated test apparatus to remove any unbound antibody or antigen in said unknown sample;

h. contacting said washed test apparatus with said antigen or antibody labeled with a radioactive isotope;

i. incubating said washed test apparatus while in contact with said antigen or antibody labeled with a radioactive isotope so as to bond said radioactive form of said unknown antibody or antigen, respectively, bonded on said test apparatus and thereby produce a radioactively traced incubated coating as a third layer;

j. washing said radioactively traced incubated coating to remove any unbonded radioactively-labeled antigen or antibody;

k. placing a control sample in contact with another incubated and washed test apparatus also prepared according to steps (a) through (d);

l. incubating said control sample while in contact with said coated test apparatus to bond any of said antibody or antigen present in said control sample as a second layer to said antibody or antigen layer on said test apparatus, respectively;

m. washing said incubated test control apparatus to remove any unbonded antibody or antigen in said control sample;

n. contacting said washed test control apparatus with a form of said antigen or antibody labeled with a radioactive isotope;

o. incubating said washed test control apparatus while in contact with said form of said antigen or antibody labeled with a radioactive isotope so as to bond said radioactive form to said coated antibody or antigen, respectively, bonded on said test apparatus and thereby produce a radioactivity traced incubated coating as a third layer;

p. washing said radioactively traced incubated coating to remove any unbonded radioactively-labeled antigen or antibody;

q. counting radiation emitted from said radioactively traced incubation coating of step (j); and r. comparing the number of counts from said coating of step (j) with the number of counts from the control sample prepared by steps (k) to (p).

2. A method as in claim 1 wherein a water wash is used in steps (g), (j), (m) and (p).

3. A method as in claim 1 wherein the apparatus is incubated at a temperature of from 35°–55° C in steps (f), (i), (n) and (o).

4. A method as in claim 1 wherein the radioactive isotope is selected from the group consisting of $I^{125}$, $I^{131}$, $P^{32}$ and tritium.

5. A method as in claim 1 wherein the radioactive form of antibody or antigen is in a purified form.

6. A method for determining the presence of a hepatitis associated antigen or its antibody in an unknown sample utilizing direct radioimmunoassay comprising:

a. contacting said unknown sample with a test apparatus having an antigen or its antibody affixed thereto as a first layer of said antigen or its antibody;

b. incubating said unknown sample while in contact with said first layer to provide a second layer of said antigen or its antibody;

c. washing said incubated layer;

d. contacting said washed layer with a radioactively traced material selected from said antigen or its antibody with the proviso
 1. if said first layer is said antigen, said radioactively traced material is also said antigen;
 2. if said first layer is said antibody, said radioactively traced material is also an antibody to said hepatitis associated antigen;

e. incubating said washed second layer while in contact with said radioactively traced material to provide a third layer;

f. washing said radioactively traced incubated layer to remove any unbonded radioactively traced material; and counting radiation emitted from said radioactively traced layer of step (f).

7. A method as in claim 6 wherein said apparatus is incubated at a temperature of from 35°–55° C in steps (b) and (e).

8. A method as in claim 7 wherein said temperature is about 45° C.

9. A method as in claim 6 which includes the additional steps of:

h. providing another test apparatus having an antigen or its antibody affixed thereto to provide a first layer of said antigen or its antibody;

i. contacting a control sample with the antigen or its antibody affixed to the test apparatus to provide a second layer of said antibody or its antigen;

j. incubating said control sample while in contact with said first layer;

k. washing said incubated layer;

l. contacting said washed layer with a radioactively traced material selected from said antigen or its antibody with the proviso
 1. if said first layer is said antigen, said radioactively traced material is also said antigen,
 2. if said first layer is said antibody, said radioactively traced material is also said antibody;

m. incubating said washed second layer while in contact with said radioactively traced material to provide a third layer;

n. washing said radioactively traced incubated layer to remove any unbonded radioactively traced material;

o. comparing the number of counts from said layer of step (f) with the number of counts from the control sample prepared by steps (i) to (n).

10. A method as in claim 6 wherein the radioactively traced material is labeled with $I^{125}$.

11. A method as in claim 6 wherein a water wash is used in steps (c) and (f).

* * * * *